United States Patent
Taneda

(10) Patent No.: US 10,444,206 B2
(45) Date of Patent: Oct. 15, 2019

(54) CHROMATOGRAPHY/MASS SPECTROMETRY DATA PROCESSING DEVICE

(71) Applicant: SHIMADZU CORPORATION, Kyoto-shi, Kyoto (JP)

(72) Inventor: Katsuyuki Taneda, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 316 days.

(21) Appl. No.: 15/586,499

(22) Filed: May 4, 2017

(65) Prior Publication Data
US 2018/0321201 A1    Nov. 8, 2018

(51) Int. Cl.
G01N 30/86    (2006.01)
G01N 30/72    (2006.01)
H01J 49/00    (2006.01)

(52) U.S. Cl.
CPC ..... *G01N 30/8679* (2013.01); *G01N 30/8631* (2013.01); *G01N 30/72* (2013.01); *G01N 30/8634* (2013.01); *G01N 30/8644* (2013.01); *G01N 30/8682* (2013.01); *H01J 49/0009* (2013.01); *H01J 49/0036* (2013.01)

(58) Field of Classification Search
None
See application file for complete search history.

(56) References Cited

U.S. PATENT DOCUMENTS

| | | | |
|---|---|---|---|
| 9,548,190 B2* | 1/2017 | Campbell | H01J 49/004 |
| 2015/0198569 A1* | 7/2015 | Baba | G01N 30/8634 |
| | | | 250/282 |
| 2016/0025691 A1* | 1/2016 | Taneda | G01N 30/8637 |
| | | | 702/23 |

FOREIGN PATENT DOCUMENTS

JP    2013-234859 A    11/2013

* cited by examiner

*Primary Examiner* — Gregory J Toatley, Jr.
*Assistant Examiner* — Terence E Stifter, Jr.
(74) *Attorney, Agent, or Firm* — Sughrue Mion, PLLC

(57) ABSTRACT

Peaks are detected on a mass chromatogram at multiple m/z ratios characterizing a target component, and the detected peaks are classified into groups according to their occurrence time. The measured mass spectrum is acquired for each group, the measured mass spectrum and standard mass spectrum of the target component are matched for each m/z, and the standard mass spectrum is normalized by multiplying it by the same scale factor for all the m/z ratios such that it does not exceed the peak intensities on the measured mass spectrum. The quantitation ion m/z peak intensity on the normalized standard mass spectrum is then examined, and if this intensity exceeds a preset threshold and the confirmation ion ratio determined based on the measured mass spectrum obtained for the target component is outside a reference range, then that target component is taken as a narrowed result candidate.

14 Claims, 5 Drawing Sheets

CHROMATOGRAPHY/MASS SPECTROMETRY DATA PROCESSING DEVICE

TECHNICAL FIELD

The present invention relates to a data processing device which processes data acquired with a chromatograph/mass spectrometer such as a gas chromatograph-mass spectrometer (GC-MS) or liquid chromatograph-mass spectrometer (LC-MS); more specifically, the invention relates to a chromatography/mass spectrometry data processing device suitable for screening analysis for a target component in samples containing many interfering components.

BACKGROUND ART

In chromatograph-mass spectrometers such as GC-MS and LC-MS, various components contained in a sample are separated by the chromatograph in the time direction, and ions originating from each of the separated components are detected. To quantitate a target component in a sample with a chromatograph-mass spectrometer, generally, a mass chromatogram at a mass/charge ratio m/z corresponding to the target component (also known as an extracted ion chromatogram) is generated, and the surface area of chromatogram peaks occurring in the vicinity of the retention time of the target component in that mass chromatogram is found. Then, referring to a calibration curve prepared in advance, the concentration, i.e. quantitative value, of the target component is computed based on the measured surface area.

For example, in tests for residual agrochemicals in foods and drinks, agrochemicals would be the target components, but such samples contain many interfering components besides the target components, and the target components and interfering components cannot be adequately separated with a chromatograph, so often, the interfering components will affect the chromatogram peaks of the target component. Specifically, if the elution time of an interfering component is close to the elution time of a target component and ions of the same mass/charge ratio (actually, ions included within a predetermined mass/charge ratio range) are produced for both the interfering component and the target component, then peaks originating from the interfering component will overlap peaks originating from the target component on the mass chromatogram at that mass/charge ratio. Furthermore, such peak overlap may cause the retention time for peaks originating from the target component to be recognized incorrectly (offset from where they actually are).

Generally, in order to confirm that a certain peak on a mass chromatogram is indeed a peak originating from a target component, in other words, in order to identify the target component, besides the retention time of the peak on a mass chromatogram at a mass/charge ratio characteristic for the target component, the ratio of signal intensities of peaks at multiple different mass/charge ratios on the mass spectrum obtained at that retention time (the so-called confirmation ion ratio) or the like is used (see Patent literature 1, etc.). However, when the influence of interfering components is great as described above, to ensure reliability of analysis, the operator would in actuality have to visually confirm each mass chromatogram and mass spectrum and determine if the influence of interfering components is or is not present.

In testing for residual agrochemicals in foods in Japan, currently, a positive list system has been adopted, with analysis of over one hundred types of residual agrochemicals being performed at once, but for a very large number analytes, the conventional technique described above is inefficient in that it takes much effort and time for an operator to perform the confirmation operation for all the target components. Thus, as a technique for improving the efficiency of the analysis operation, the method is also used whereby thresholds are established in advance for the quantitative value (concentration) and confirmation ion ratio for each of the target components, these are narrowed down to only those components for which the quantitative value or confirmation ion ratio obtained through actual analysis exceeds the aforementioned threshold, i.e., components which may have been influenced by interfering components, and mass chromatograms and mass spectra are confirmed one by one only for those components.

In terms of specific methods, for the analysis of residual agrochemicals in foods, the method of classifying target components into three groups (G1) through (G3) as follows is known in the prior art.

(G1): Group of components for which confirmation operations are unnecessary because the component is clearly not contained in the analyte in question or because the measured quantitative value is at or below the threshold.

(G2): Group of components which are clearly present at a high concentration because the measured quantitative value exceeds the threshold and the confirmation ion ratio is at or below the threshold.

(G3): Group of components for which it is unclear whether the component is the assumed target component or not and for which additional confirmation is required because the measured quantitative value exceeds the threshold but the confirmation ion ratio also exceeds the threshold.

If classification of components as described above can be performed with high accuracy, it will suffice to confirm the mass chromatogram and mass spectrum only for components classified as (G3), so operator effort and time can be greatly reduced as compared to the case where the same confirmation operation is performed for all the detected components. However, if peaks originating from interfering components overlap peaks on the mass chromatogram at the mass/charge ratio for quantitative calculation (the so-called quantitation ion mass/charge ratio) and the peak area increases, then the quantitative values computed based on peak area will be inflated, and components which should properly be classified as (G1) may end up being erroneously classified as (G3). Furthermore, if it becomes impossible to detect peaks near the location of the target component's retention time due to overlap of large peaks originating from interfering components, or the like, then components which should properly be classified as (G2) or (G3) may end up being erroneously classified as (G1).

Here, examples of cases where erroneous classification is performed will be described based on FIG. 6.

Here, data has been acquired with $M_1$ being specified as the quantitation ion mass/charge ratio and with $M_2$ and $M_3$ being specified as confirmation ion mass/charge ratios for confirmation ion ratio calculation. Furthermore, it will be assumed that the standard mass spectrum corresponding to the target component (the standard mass spectrum) is substantially the same as the measured mass spectrum of data A shown in FIG. 6 at (a). Moreover, there are two conditions for being classified as (G3): (i) the concentration corresponding to the intensity of a peak characteristic of the target component observed on a mass chromatogram at mass/charge ratio $M_1$ (hereinafter, such a mass chromatogram will be denoted as mass chromatogram ($M_1$)) is at or above a reference value (10 ppb), and (ii) the confirmation ion ratio is outside the reference range (at or above a threshold value).

In data A shown in FIG. 6 at (a), the concentration and confirmation ion ratio for the peak originating from the target component designated by the downward facing arrow on mass chromatogram ($M_1$) are calculated without being affected by peaks originating from interfering components appearing on either side of that peak. Thus, the concentration exceeds the reference value and the confirmation ion ratio is within the reference range, so the target component of interest is clearly present and is thus excluded from the narrowed set. In this case, the target component is classified as (G2).

On the other hand, in data B shown in FIG. 6 at (b), the peak originating from the target component on the mass chromatogram ($M_1$) is overlapped by the large peak originating from an interfering component present immediately before it. Thus, identification of the target component is judged not based on the original retention time but on a peak originating from a different component with an offset retention time as shown by the downward facing arrow. In this case, the computed concentration is 5 ppb, which is lower than the actual concentration (15 ppb) of the target component and is below the reference value, so the target component in question is erroneously deemed to not require confirmation and is excluded from the narrowed set. In this case, the target component is classified as (G1).

In data C shown in FIG. 6 at (c), although the target component of interest is not contained, a peak originating from a different component with a similar retention time is detected on the mass chromatogram ($M_1$), and identification of the target component is performed using the concentration and confirmation ion ratio based on that peak. As a result, the target component is classified as (G3) and is included in the narrowed set even though there is clearly no need for such inclusion to begin with.

Moreover, in data D shown in FIG. 6 at (d), the retention time of the target component of interest and of one interfering component are substantially the same, so this interfering component inflates the intensity of the peak originating from the target component. As a result, the computed concentration becomes a concentration higher than the actual concentration (5 ppb) of the target component, and as a result, the target component is classified as (G3) and is included within the narrowed set even though there is clearly no need for such inclusion to begin with.

In this way, in the above examples, based on the actual concentration of the target component, both data A and data B should be included in the narrowed set, but data B ends up being excluded, and conversely, data C and data D should by nature be excluded from the narrowed set, but end up being included in the narrowed set. Namely, when evaluating whether or not the component is to be included in the narrowed set based on actually measured data, false negatives and false positives occur, leading to a reduction in screening accuracy and to unnecessary effort being expended on the screening.

If a mass/charge ratio not affected by interfering components could be selected as the quantitation ion mass/charge ratio, it would be possible to avoid the problems described above. However, the interfering components which are present differ depending on the type of food which is the analyte, the method of pretreatment for analysis, the type of liquid phase used in liquid chromatography, and the like. Thus, it is practically rather difficult to select a mass/charge ratio not affected by interfering components in advance as the quantitation ion mass/charge ratio.

PRIOR ART DOCUMENTS

Patent Documents

[Patent literature 1] Japanese Unexamined Patent Application Publication 2013-234859 (Paragraph (0006))

SUMMARY OF INVENTION

Problem to be Solved by the Invention

The present invention was made to resolve the aforesaid problem, its object being to provide a chromatography/mass spectrometry data processing device which is able to reduce the volume of operations carried out by an operator, etc. for confirming whether or not there is influence of an interfering component when determining the presence of or quantitating a target component in a sample having admixed interfering components, and which is able to determine the need for such operations with high accuracy.

Means for Solving the Problem

The present invention, made to resolve the above problem, is a chromatography/mass spectrometry data processing device which performs analytical processing of data obtained by separating components in a sample in the time direction with a chromatograph and then repeatedly performing mass analysis over a predetermined mass/charge ratio range, characterized in that it comprises:

a) an information storage unit which, for each target component, stores a retention time, standard mass spectrum, multiple characteristic mass/charge ratios which are mass/charge ratios at which characteristic peaks appear on said standard mass spectrum, and an intensity threshold for evaluating peak intensity at a representative mass/charge ratio among said multiple characteristic mass/charge ratios;

b) a measured mass spectrum extraction unit which, for a target component of interest, classifies peaks detected on a mass chromatogram at said multiple characteristic mass/charge ratios generated on the basis of data obtained through actual measurement, into one or multiple peak groups according to the occurrence time thereof, and acquires a measured mass spectrum obtained at the appearance time of the peak tops of peaks contained in at least one of those peak groups;

c) a standard mass spectrum scaling unit which matches the measured mass spectrum extracted by said measured mass spectrum extraction unit with the standard mass spectrum corresponding to said target component of interest at each mass/charge ratio, and scales up or scales down the peak intensities of said standard mass spectrum uniformly across the entirety of the mass/charge ratios so as not to exceed the intensities of the peaks on said measured mass spectrum; and d) a component selection unit which, on the standard mass spectrum which has been scaled up or scaled down by said standard mass spectrum scaling unit, evaluates whether or not the peak intensity at the representative mass/charge ratio corresponding to said target component of interest exceeds the intensity threshold corresponding to that target component, and uses the fact that it does exceed the corresponding intensity threshold as a condition for selecting that target component as a component whereof the presence is uncertain.

Here, the chromatograph is, for example, a liquid chromatograph or a gas chromatograph.

In the chromatography/mass spectrometry data processing device according to the present invention, a retention time, standard mass spectrum, multiple characteristic mass/charge ratios and an intensity threshold are stored in advance in the information storage unit for each target component to be measured. The standard mass spectrum can be obtained, for example, by measuring a standard sample under conditions unaffected by interfering components. Furthermore, generally, the multiple characteristic mass/charge ratios are quantitation ion and confirmation ion mass/charge ratios, of which the quantitation ion mass/charge ratio can be used as the representative mass/charge ratio.

The measured mass spectrum extraction unit references the retention time of the target component of interest, and classifies the peaks detected on the mass chromatogram at multiple characteristic mass/charge ratios generated on the basis of data obtained through actual measurement, into one or multiple peak groups according to the occurrence time thereof. In cases where an interfering component of high concentration is present in the vicinity of the occurrence time of the target component and the characteristic mass/charge ratio of the target component and the mass/charge ratio of the interfering component match, the peak originating from the target component may overlap the peak originating from the interfering component on the mass chromatogram, making it impossible to detect the peak originating from the target component. But even in such a situation, it will normally not be the case that the peak on the mass chromatogram cannot be detected at any of the multiple characteristic mass/charge ratios established for the target component. Thus, a peak originating from the target component will be detected on the mass chromatogram at least at one of the multiple characteristic mass/charge ratios corresponding to the target component. This makes it possible to obtain a peak group containing a peak originating from the target component even when interfering components are present, and makes it possible to obtain a measured mass spectrum near the occurrence time of the target component.

The standard mass spectrum scaling unit reads the standard mass spectrum corresponding to the target component of interest from the storage unit, matches the standard mass spectrum with the aforementioned measured mass spectrum at each mass/charge ratio, and scales up or scales down the peak intensities of the standard mass spectrum so as not to exceed the intensities of the peaks on the measured mass spectrum uniformly, i.e., by multiplying by a constant scale factor, across the entirety of the mass/charge ratios. The component selection unit then evaluates whether or not the component is a component whereof the presence is uncertain using, as a condition of evaluation, whether or not the peak intensity at the representative mass/charge ratio corresponding to the target component of interest exceeds the intensity threshold corresponding to that target component on the scaled-up or scaled-down standard mass spectrum, rather than on the measured mass spectrum.

If the target component of interest is completely unaffected by interfering components, the measured mass spectrum can be represented using a constant factor of the standard mass spectrum. On the other hand, when the influence of interfering components is present, the peak intensity of the measured mass spectrum increases by an amount corresponding to the interfering components. However, even in such a case, as discussed above, it will not normally be the case that peaks at all the characteristic mass/charge ratios will be affected by interfering components, so there is a high likelihood that a peak at least at one of the characteristic mass/charge ratios will be a peak originating from the target component unaffected by interfering components.

For example, if an interfering component is present at substantially the same retention time as the retention time of the target component and the representative mass/charge ratio corresponding to that target component matches the mass/charge ratio for the interfering component, then even if hardly any target component is actually present, a peak originating from the interfering component will appear at the representative mass/charge ratio thereof in the measured mass spectrum. However, at another characteristic mass/charge ratio which is completely or largely unaffected by the aforementioned interfering component in the measured mass spectrum, the peak intensities will be small, and on a standard mass spectrum scaled up or scaled down at a scale factor determined so as not to exceed those peak intensities, the influence of the interfering component will be relatively small. Thus, if peak intensity is evaluated at the representative mass/charge ratio on the standard mass spectrum which has been scaled up or scaled down, a more appropriate evaluation can be carried out, from which the influence of overlap of interfering components has been eliminated.

However, even when it is certain that the target component is contained, the aforementioned component selection unit will determine that the aforementioned peak intensity exceeds the intensity threshold. Thus, the chromatography/mass spectrometry data processing device according to the present invention is more preferably configured such that the component selection unit selects the target component as a component whereof the presence is uncertain if the peak intensity at the representative mass/charge ratio corresponding to said target component of interest exceeds the intensity threshold corresponding to that target component and if the confirmation ion ratio, which is the ratio between the peak intensity at the representative mass/charge ratio and the intensity of peaks at other characteristic mass/charge ratios, is also outside a predetermined range.

Furthermore, in the chromatography/mass spectrometry data processing device according to the present invention, if it has finally been established that the target component is one whereof the presence is uncertain, it is preferable to present that target component to the analyst and prompt for visual confirmation of the measured mass spectrum, mass chromatogram, etc.

Thus, one embodiment of the chromatography/mass spectrometry data processing device according to the present invention is suitably configured such that the device further comprises a display processing unit which generates a table listing abundances, or indicator values reflecting abundances, of multiple target components for each sample, and displays the table on a screen of a display unit, wherein the display processing unit displays the abundances or indicator values reflecting abundances of target components selected as components whereof the presence is uncertain by said component selection unit in a manner distinguishable from the abundances or indicator values reflecting the abundances of other target components.

Here, the indicator value reflecting the abundance of a target component is for example the chromatogram peak area or peak height.

This configuration makes it possible for the operator (analyst) to ascertain at a glance the target components for which the mass chromatogram, etc. should be visually confirmed based on a table listing the abundances, or indicator values reflecting abundances, of multiple target components for each sample.

Furthermore, the chromatography/mass spectrometry data processing device according to the present invention may be configured such that it further comprises a display processing unit which, for a target component selected as a component whereof the presence is uncertain, displays a mass chromatogram at the representative mass/charge ratio corresponding to that target component on a screen of a display unit. Moreover, the chromatography/mass spectrometry data processing device according to the present invention may be configured such that it further comprises a display processing unit which, for a target component selected as a component whereof the presence is uncertain, displays the measured mass spectrum acquired by said measured mass spectrum extraction unit on a screen of a display unit.

The mass chromatogram or mass spectrum is suitably associated with the quantitative value display section or the quantitative values therein in the table of the aforementioned list display, and is displayed in a pop-up window which opens automatically when that section or the value is clicked with a pointing device such as a mouse or when a cursor is placed over the section or value using a pointing device. Such a configuration allows the mass chromatogram and mass spectrum which is to be visually confirmed by the operator to be displayed through a simple operation, reducing the effort involved in the operations performed by the operator to confirm the mass chromatogram and mass spectrum.

Furthermore, in the chromatography/mass spectrometry data processing device according to the present invention, the display processing unit may display a standard mass spectrum which has been scaled up or scaled down by the standard mass spectrum scaling unit along with the measured mass spectrum on a screen of a display unit.

This makes it possible for the operator to confirm the standard mass spectrum of the target component along with the measured mass spectrum and to easily evaluate if there is influence of interfering components in the measured mass spectrum.

Effect of the Invention

With the chromatography/mass spectrometry data processing device according to the present invention, when investigating if a target component is contained in a sample or not or when quantitating a target component, even in cases where a peak originating from the target component on a mass chromatogram cannot be detected at the appropriate retention time or when the intensity of a peak originating from a target component is inflated above what it actually is, it is possible to accurately select only the components whereof the presence is uncertain, excluding components which are clearly contained in the sample or which are conversely clearly not contained. In other words, it is possible to accurately separate out components for which the mass chromatogram and mass spectrum actually need to be visually confirmed by an operator. The burden on the operator involved in such confirmation operations can thus be reduced, making it possible to increase the efficiency of analysis operations in cases such as residual agrochemical testing, where quantitation of numerous target components is performed on numerous specimens.

DETAILED DESCRIPTION OF THE EXEMPLARY EMBODIMENTS

Figure 1:
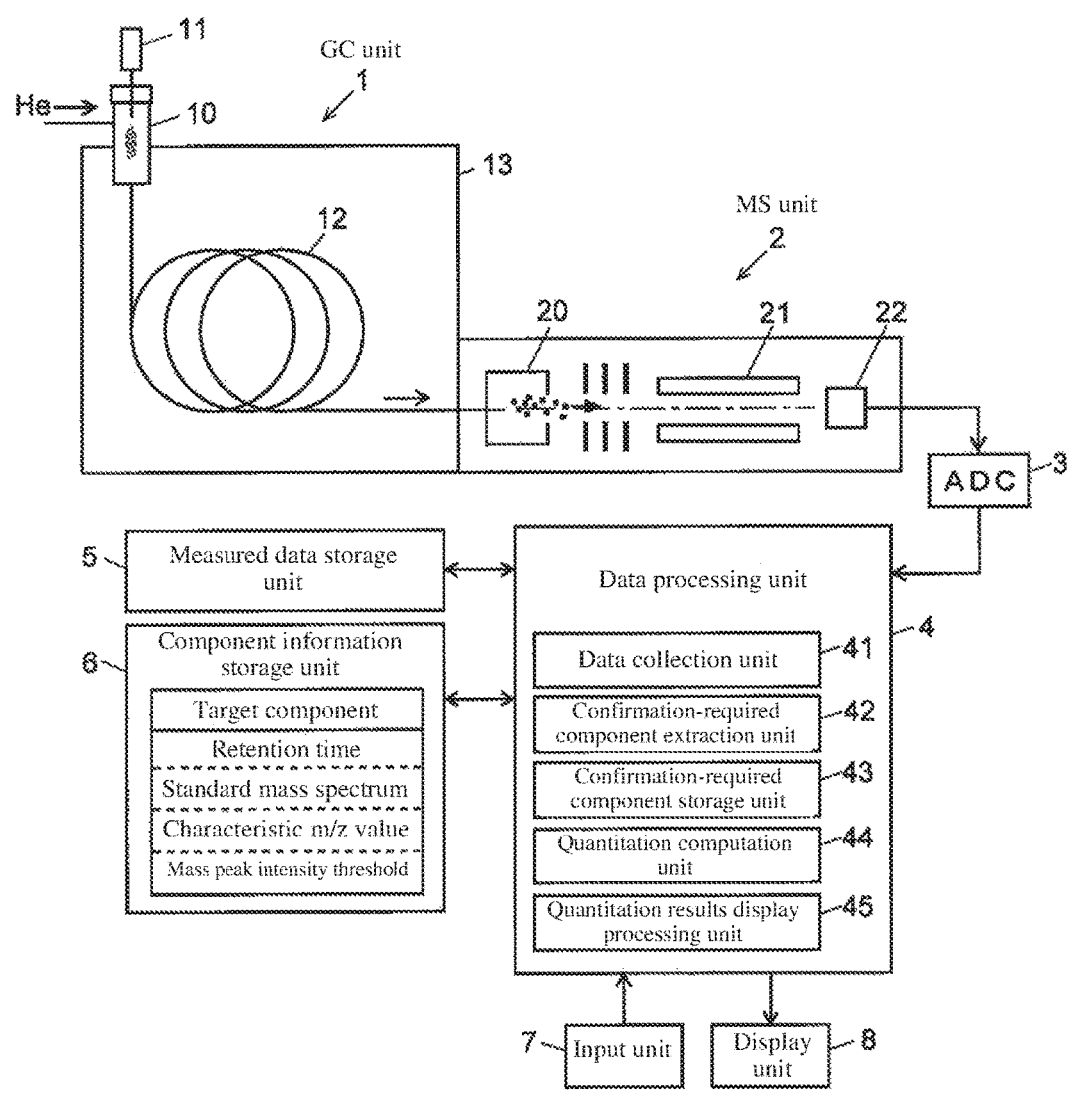
FIG. 1 An overall diagram of an embodiment example of a GC-MS employing a chromatography/mass spectrometry data processing device according to the present invention.

An embodiment example of a GC-MS employing a chromatography/mass spectrometry data processing device according to the present invention will be described below with reference to the appended drawings.

The GC-MS of this embodiment example comprises a GC unit 1 including a sample gasification chamber 10, injector 11, column 12, and column oven 13 which houses the column 12, and an MS unit 2 including an ion source 20, quadrupole mass filter 21 and ion detector 22, with the detection signals generated by the ion detector 22 being converted to digital data in A/D converter 3 and inputted into data processing unit 4.

In the GC unit 1, a carrier gas such as helium is supplied through the sample gasification chamber 10 into the column 12 at a constant flow rate. Small amounts of sample are injected from the injector 11 into the sample gasification chamber 10 at a predetermined timing based on instructions from an unillustrated control unit, whereupon the sample is instantaneously gasified and carried by the carrier gas flow into the column 12. While passing through the column 12, which is temperature-regulated by the column over 13, the components contained in the sample are separated and flow out from the outlet of the column 12 in temporally offset fashion.

The sample gas which flows out from the column 12 is introduced into the ion source 20 in MS unit 2, and the component molecules contained in the sample gas are ionized, for example, through electron ionization. The generated ions are introduced into the quadrupole mass filter 21, and only ions having a specific mass/charge ratio m/z, according to the voltage applied to the quadrupole mass filter 21, selectively pass through and reach the ion detector 22. An unillustrated quadrupole driving unit repeatedly sweeps the voltage applied to the quadrupole mass filter 21 over a predetermined voltage range, thereby performing mass scanning across a predetermined mass/charge ratio range. In this way, in the MS unit 2, scanning measurement over a predetermined mass/charge ratio range is performed on the sample gas successively introduced with the passage of time, and data having mass/charge ratio, time and signal intensity as its dimensions is inputted through the analog-digital conversion unit (ADC) 3 into the data processing unit 4.

The data processing unit 4 comprises, as functional blocks, a data collection unit 41, confirmation-required component extraction unit 42, confirmation-required component storage unit 43, quantitation computation unit 44, quantitation results display processing unit 45, etc. A measured data storage unit 5, component information storage unit 6, input unit 7 and display unit 8 are connected to the data processing unit 4. The retention time, standard mass spectrum, characteristic mass/charge ratio values (normally, quantitation ion and confirmation ion mass/charge ratio values), mass peak intensity threshold for evaluating peak intensity, etc., are stored in advance in the component information storage unit 6 for all the target components which one wants to quantitate or confirm the presence or absence of.

The data collection unit 41 collects data inputted when measurement is performed as described above and stores it in measured data storage unit 5. After completion of measurement, when an instruction to perform data analysis processing (target quantitation processing) is received via the input unit 7, the confirmation-required component extraction unit 42 reads the data to be analyzed from the measured data storage unit 5, reads information such as retention time relating to the target components from the component information storage unit 6, and executes the distinctive processing described later to extract components requiring visual confirmation by the operator. The extracted components are stored in confirmation-required component storage unit 43. The quantitation computation unit 44 performs quantitation of target components based on a mass chromatogram at the quantitation ion or confirmation ion mass/charge ratio. The quantitation results display processing unit 45 displays the quantitative analysis results on display unit 8.

The data processing unit 4 and the unillustrated control unit are in substance a personal computer, and the functions of the confirmation-required component extraction unit 42, etc. can be implemented by executing specialized control and processing software preinstalled on the computer.

In the GC-MS of this embodiment example, prior to the quantitation computation by the quantitation computation unit 44, the confirmation-required component extraction unit 42 classifies the numerous target components contained in a single sample into the three groups (G1) through (G3) described above. To repeat, groups (G1) through (G3) are as follows.

(G1): Group of components for which confirmation operations are unnecessary because the component is clearly not contained in the analyte in question or because the measured quantitative value is at or below the threshold.

(G2): Group of components which are clearly present at a high concentration because the measured quantitative value exceeds the threshold and the confirmation ion ratio is at or below the threshold.

(G3): Group of components for which it is unclear whether the component is the assumed target component or not and for which additional confirmation is required because the measured quantitative value exceeds the threshold but the confirmation ion ratio also exceeds the threshold.

Figure 2:
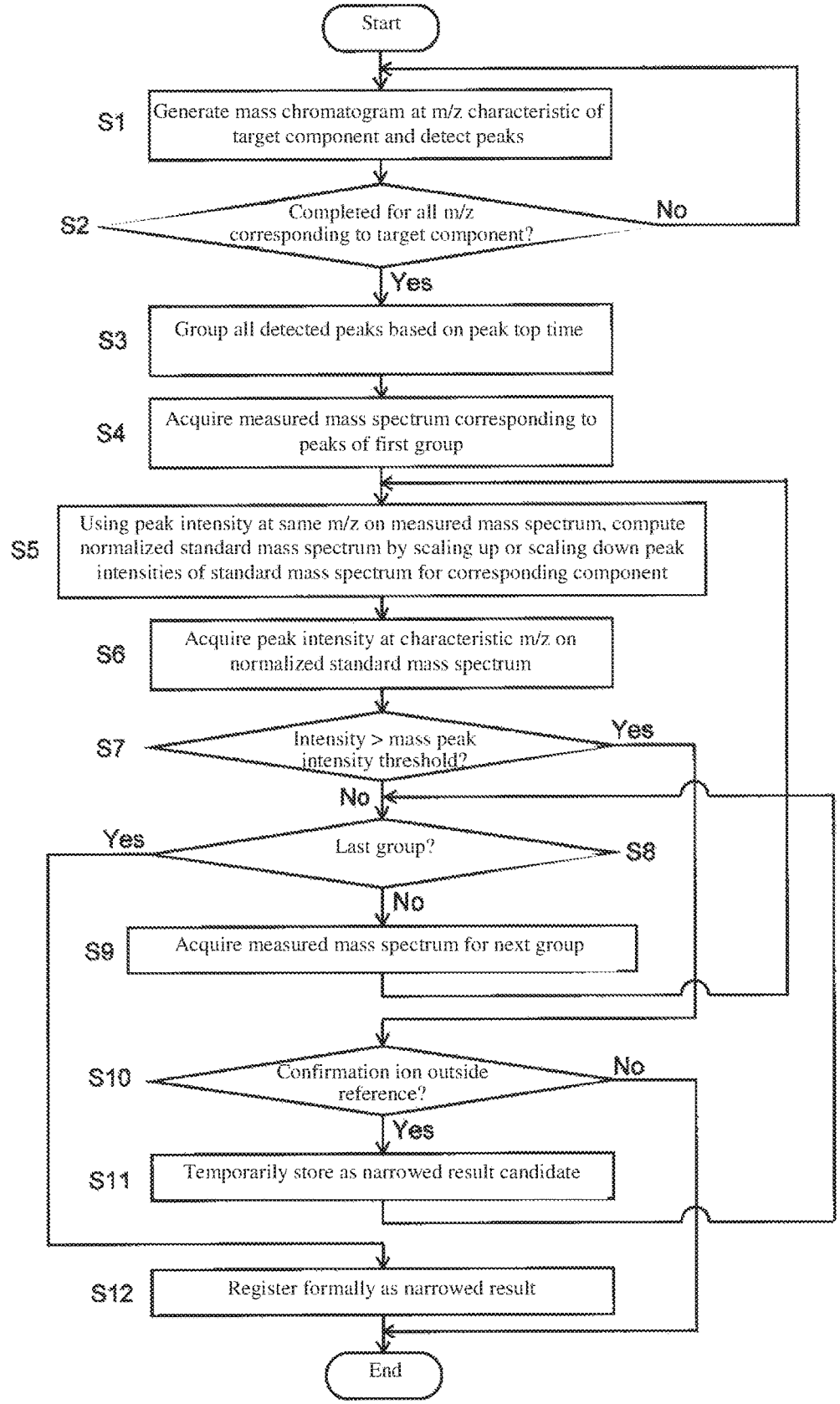
FIG. 2 A flow chart illustrating the data processing operations in a GC-MS in this embodiment example.
Figures 4, 5:
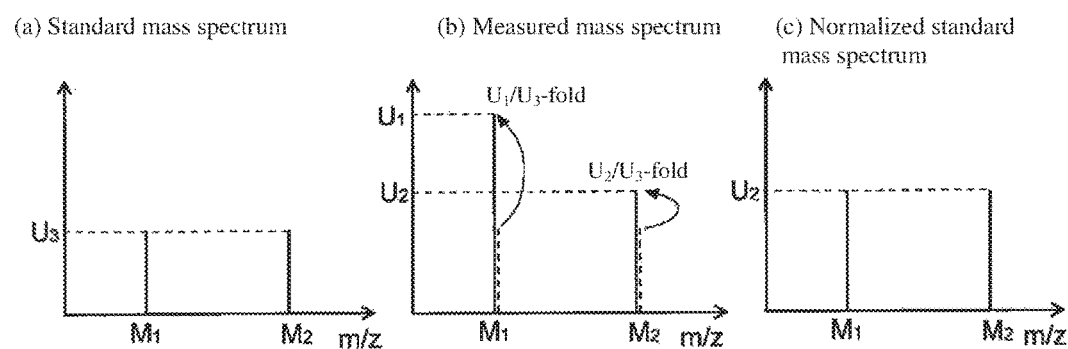
FIG. 4 A schematic intended to explain the data processing in the GC-MS of this embodiment example.
FIG. 5 A drawing illustrating an example of the quantitation results displayed in the GC-MS of this embodiment example.
Figure 6:
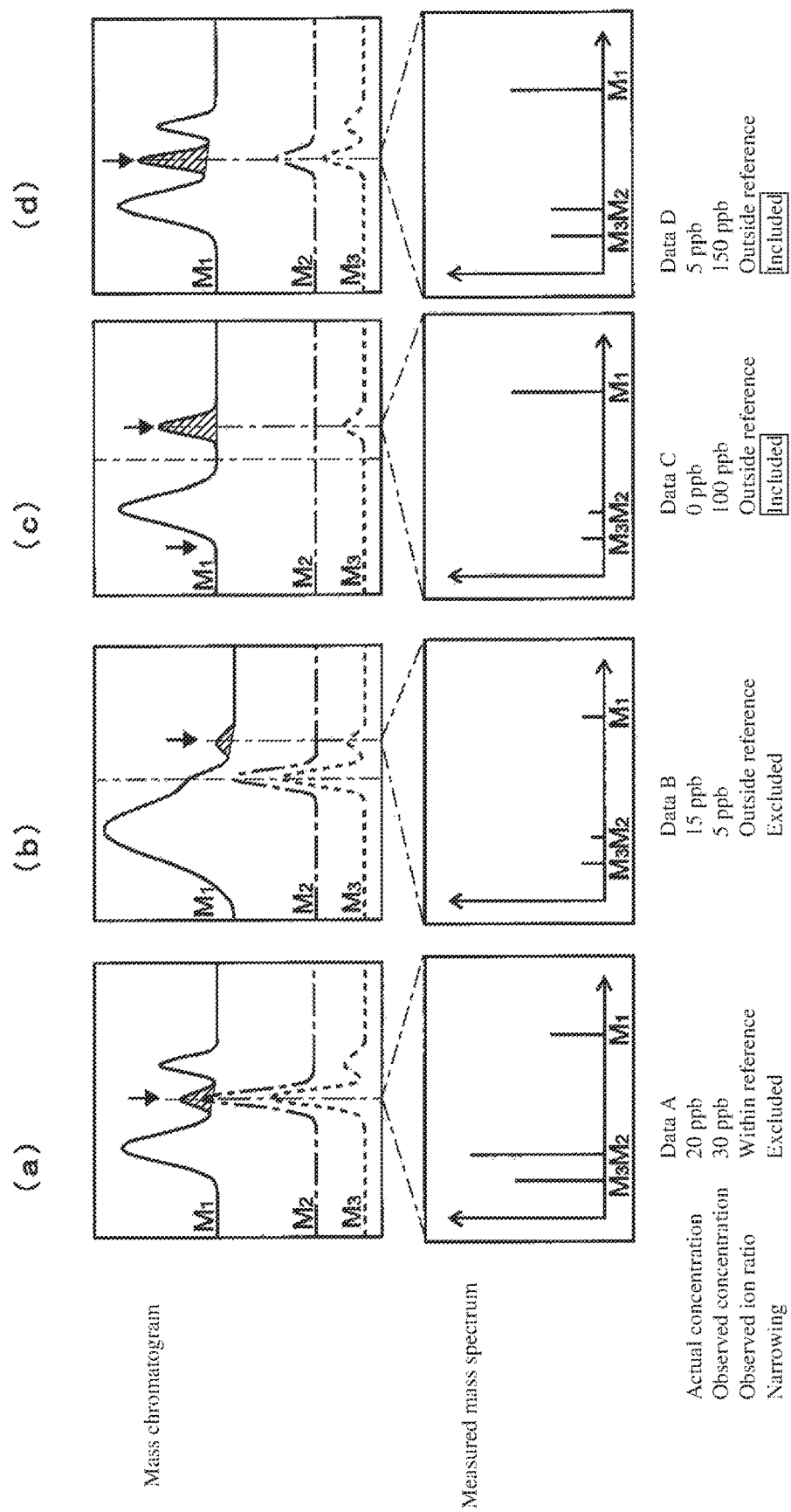
FIG. 6 A drawing showing an example of a mass chromatogram and measured mass spectrum near the retention time of a target component of interest.

In the GC-MS of this embodiment example, the confirmation-required component extraction unit 42 performs the distinctive data processing described below, thereby improving the accuracy of classification, minimizing needless work by the operator, and reducing failures to detect target components. FIG. 2 is a flow chart of the data processing operations for classifying one target component of interest; FIG. 4 is an explanatory drawing for the case where data processing is performed in the GC-MS of this embodiment example on the data shown in FIG. 6; and FIG. 5 is a schematic intended to explain the data processing in the GC-MS of this embodiment example.

When the start of processing for classifying the target component of interest into one of the aforementioned three groups is instructed, the confirmation-required component extraction unit 42 reads the retention time corresponding to that target component from the component information storage unit 6, and reads the measured data obtained in a predetermined time range, with an appropriate time band provided before and after that retention time, from the measured data storage unit 5. A mass chromatogram within the predetermined time range is then generated for one characteristic mass/charge ratio corresponding to the target component. Subsequently, peaks are detected in that mass chromatogram according to a predetermined peak detection algorithm (step S1). As a specific example, the case where data A shown in FIG. 3 at (a) is the object of processing will be considered. In this case, assuming the characteristic mass/charge ratio is $M_1$, mass chromatogram ($M_1$) represented by the solid line in the top part of FIG. 3 at (a) is generated and three peaks are detected.

Figure 3:
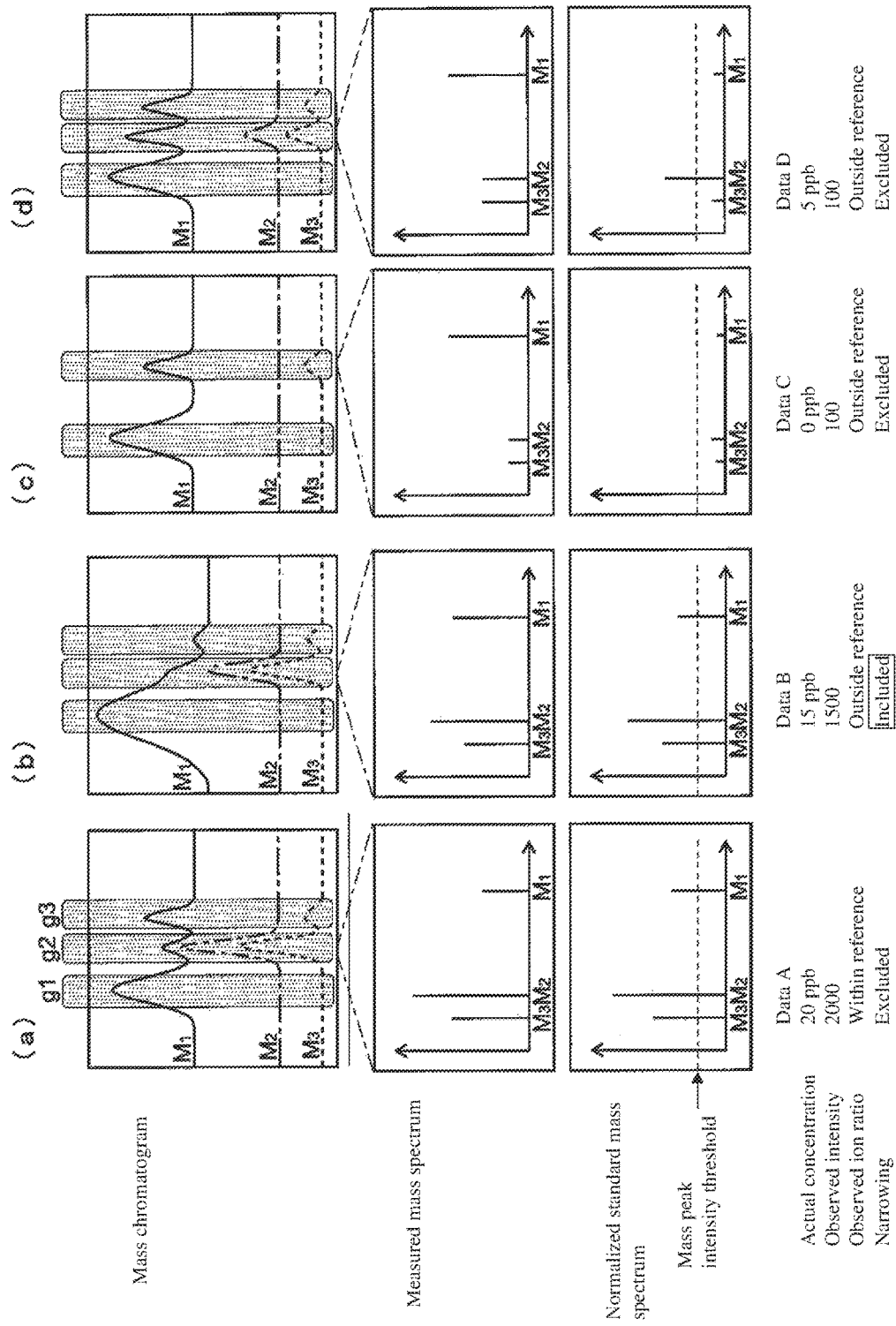
FIG. 3 An explanatory drawing for the case where data processing is performed in the GC-MS of this embodiment example on the data shown in FIG. 6.

Next, it is determined if the processing of step S1 has been carried out for all the characteristic mass/charge ratios registered in the component information storage unit 6 for the target component (step S2), returning to step S1 if there is a characteristic mass/charge ratio which has not been processed yet. Therefore, by repeating steps S1 and S2, peaks are detected for all the mass chromatograms at multiple characteristic mass/charge ratios corresponding to the target component. In the example of FIG. 3 at (a), $M_2$ and $M_3$ have been registered in addition to $M_1$ as characteristic mass/charge ratios corresponding to the target component, so mass chromatograms at those mass/charge ratios $M_2$ and $M_3$ are generated and the peaks in the respective mass chromatograms are detected. As a result, one peak is detected in mass chromatogram ($M_2$) and two peaks are detected in mass chromatogram ($M_3$).

The time of occurrence of the peak tops of peaks obtained on the multiple mass chromatograms are then compared, and one or multiple peaks with a time difference within an allowable time range are assumed to be peaks originating from the same component and are grouped together (step S3). In the example of FIG. 3 at (a), at total of six peaks have been detected for the three mass chromatograms, which are divided into three groups: g1, g2 and g3.

Then, one of the peak groups, for example, the peak group with the earliest occurrence time, is selected, and the measured mass spectrum which was obtained at the time corresponding to the peak top of one peak in that peak group is acquired from the measured data storage unit 5 (step S4). When multiple peaks are contained within a peak group, for example, one may select the peak exhibiting the greatest signal intensity and find the measured mass spectrum which was obtained at the time corresponding to the peak top of that peak. Using this measured mass spectrum, the peak intensities of the standard mass spectrum associated with the target component are normalized. Specifically, peaks on the standard mass spectrum are matched with the measured mass spectrum for each mass/charge ratio, and the intensities of the peaks on the standard mass spectrum are scaled up or scaled down uniformly, i.e., using the same scale factor, across the entire mass/charge ratio range so as not to exceed the respective peak intensities on the measured mass spectrum. The standard mass spectrum which has been scaled up or scaled down shall be referred to as normalized standard mass spectrum (step S5).

The processing of step S5 above will be described in detail using FIG. 4. To simplify the description, it will be assumed here that two peaks of the same signal intensity $U_3$ are present on the standard mass spectrum, as shown in FIG. 4 at (a). Furthermore, it will be assumed that the peaks on the measured mass spectrum corresponding to the aforesaid two peaks have signal intensities $U_1$ and $U_2$, as shown in FIG. 4 at (b). For normalization of the standard mass spectrum, it is necessary to determine the ratio (scale factor) of the peak intensity on the measured mass spectrum to the peak intensity on the standard mass spectrum for the mass/charge ratios of all the peaks present on the standard mass spectrum of the target component, and then find the smallest ratio (smallest scale factor) among them. In the example of FIG. 4, $U_1/U_3 > U_2/U_3$, so the smallest scale factor is $N=U_2/U_3$, and the signal intensity of each peak on the standard mass spectrum is scaled up or down by multiplying by this smallest scale factor N (see FIG. 4 at (c)) to obtain the normalized standard mass spectrum.

Considering the possibility that the intensities of peaks on the measured mass spectrum may be increased relative to the standard mass spectrum on account of interfering components, it can be said that the mass/charge ratio for which the aforementioned scale factor is smallest is the mass/charge ratio with the least influence of interfering components at the measurement time point when the measured mass spectrum was obtained. Generally, it is likely that there will be no influence of interfering components for at least some of the mass/charge ratios, so the smallest scale factor can be viewed as a scale factor which reflects not the influence of interfering components but purely the component concentration and difference in detection sensitivity and the like. Therefore, the normalized standard mass spectrum can be said to be a mass spectrum on which the peak intensities have been corrected so as to reflect component concentration and differences in detection sensitivity and the like based on the measured mass spectrum obtained at that measurement time point.

Next, the signal intensity value of the peak for a representative mass/charge ratio (normally, the quantitation ion mass/charge ratio) is found on the aforesaid normalized standard mass spectrum, and it is evaluated whether or not this intensity value exceeds the mass peak intensity threshold which has been established for the target component (step S6, S7). If it does exceed the mass peak intensity threshold, it is possible that the target component is contained, and so the flow proceeds from step S7 to step S10, the confirmation ion ratio is calculated based on the peak intensity at the quantitation ion mass/charge ratio and peak intensity at the confirmation ion mass/charge ratios, and it is evaluated if the confirmation ion ratio is outside a predefined reference range. If it is outside the reference range, then that target component is stored temporarily as a narrowed result candidate (step S11), and the flow returns to step S8, described later. The term "narrowing" here signifies selecting or extracting a target component to be classified as group (G3).

If it was determined in step S7 that the mass peak intensity threshold was not exceeded, then it is determined if the peak group currently being processed is the last peak group that was obtained for the target component (step S8), and if it is not the last peak group, then the next peak group still unprocessed is selected, the measured mass spectrum obtained at the peak top time is acquired (step S9), and the flow returns to step S5. Normalization of the standard mass spectrum of the target component is thereby performed again using the measured mass spectrum obtained for the next peak group. The signal intensity value of the peak corresponding to the representative mass/charge ratio on the normalized standard mass spectrum determined as a result is then obtained, and it is evaluated whether or not this intensity value exceeds the mass peak intensity threshold which has been established for the target component.

Therefore, by means of the processing of steps S5 through S10, if at least one peak evaluated as Yes in step S7 is found among the peak groups obtained for a single target component, and the confirmation ion ratio computed for it is outside the predefined reference range, then the target component in question is stored temporarily as a narrowed result candidate. Conversely, if not a single peak evaluated as Yes in step S7 is present among the peak groups, or if a peak evaluated as Yes in step S7 is present but the confirmation ion ratio is within the reference range, then the target component in question does not become a narrowed result candidate and the processing is terminated. This means that the target component being processed here would be classified as group (G2).

If the decision in step S8 was Yes, it means evaluation of all the peak groups obtained for the target component has been completed, and thus the target component which is being temporarily stored at that time as a narrowed result candidate is formally stored in the confirmation-required component storage unit 43 as the narrowed result (step S12). Here, if a target component was considered as a temporary narrowed result candidate, it means that the target component in question would be classified as group (G3), and if a target component was not considered as a temporary narrowed result candidate, then the target component being processed would be classified as group (G2).

For the data A shown in FIG. 3 at (a), the processing of step S5 and subsequent is performed on the three peak groups g1, g2 and g3 divided as described above. In this example, in all three peak groups g1, g2 and g3, the peak intensity for the representative mass/charge ratio M1 in the normalized standard mass spectrum exceeds the mass peak intensity threshold. Thus, this target component is considered as a narrowed result candidate. Furthermore, in the measured mass spectrum obtained for peak group g2, there is no influence of peaks originating from the interfering components contained in peak groups g1 and g3, so the confirmation ion ratio is within the reference range, and as a result, this target component is excluded from the narrowed set and is classified as group (G2).

For data B shown in FIG. 3 at (b), two peaks are detected in mass chromatogram ($M_1$), one peak in mass chromatogram ($M_2$), and two peaks in mass chromatogram ($M_3$). Grouping these peaks yields three peak groups, just as in the example shown in FIG. 3 at (a).

On the other hand, in the measured mass spectrum obtained for peak group g2, the peak at mass/charge ratio $M_1$ shows substantial influence of interfering components, and the intensity of this peak is inflated accordingly. The amount of this inflation is reduced through normalization based on the peak intensities at mass/charge ratios $M_2$ and $M_3$, and in the normalized standard mass spectrum, the influence of interfering components on the peak at $M_1$ is significantly reduced, but the peak intensity still exceeds the mass peak intensity threshold, so this target component is considered as a narrowed result candidate. However, the peak at mass/charge ratio $M_1$ has increased intensity under influence of interfering components, so the confirmation ion ratio is not within the reference range. As a result, this target component is included within the narrowed set and is classified as group (G3). Namely, although the peak originating from the target component does not have a clear peak shape due to the influence of interfering components in mass chromatogram ($M_1$), it can be reliably included in the narrowed set without being left out therefrom as in the conventional method.

For data C shown in FIG. 3 at (c), two peaks are detected in mass chromatogram ($M_1$) and one peak is detected in mass chromatogram (M₃), while no peaks are detected in mass chromatogram (M₂). Grouping these peaks yields two peak groups. In the measured mass spectra corresponding to both peak groups, the intensity of the peak for mass/charge ratio $M_2$ is nearly zero, so the smallest scale factor becomes very small, and in the normalized standard mass spectrum, the peak intensity for mass/charge ratio $M_1$ is below the mass peak intensity threshold. As a result, this target component is excluded from the narrowed set and is classified as group (G1).

For data D shown in FIG. 3 at (d), three peaks are detected in mass chromatogram (M₁), one peak in mass chromatogram (M₂), and two peaks in mass chromatogram (M₃). Grouping these peaks yields three groups, just as in the example shown in FIG. 3 at (a). However, in this case, the peak contained in group g2 originates from an interfering component and not from the target component, and the peak pattern of the measured mass spectrum differs greatly from the standard mass spectrum for the target component. As a result, the peak intensity for mass/charge ratio $M_1$ in the normalized standard mass spectrum becomes small, being below the mass peak intensity threshold. This target component is thus excluded from the narrowed set and is classified as group (G1).

In this way, through the data processing described above, cases such as data C and data D, which would be erroneously classified into the narrowed set under conventional methods, can be reliably excluded from the narrowed set.

The flow chart shown in FIG. 2 illustrates the processing for classifying one target component in a sample into one of the groups (G1), (G2) or (G3), but repeating this allows numerous target components within a sample to be appropriately classified. Furthermore, as a result, target components whereof the presence is uncertain due mainly to the influence of interfering components are narrowed down, and the measured mass chromatogram and mass spectrum can be displayed only for those narrowed target components so that they can be easily confirmed by an operator.

Specifically, in the GC-MS of this embodiment example, the quantitation results display processing unit 45 performs distinctive display as follows. FIG. 5 is a drawing illustrating an example of the quantitation results displayed on display unit 8. In FIG. 5, "specimen" refers to a sample, and the results of quantitating numerous target components (components A, B, C, ... ) for each of numerous samples (specimens a, b, c, ... ) , i.e. the quantitative values (concentration values), are displayed in list format.

The quantitative values displayed here have been computed based on the peak area on a mass spectrum at the quantitation ion or confirmation ion mass/charge ratios corresponding to the target component in quantitation computation unit 44. The processing performed by the confirmation-required component extraction unit 42 describe above computes quantitative values for target components classified into all of the groups (G1), (G2) and (G3), but in the display shown in FIG. 5, the quantitative values for target components classified as group (G3), i.e., those included in the narrowed set, are indicated using characters of a different color or different font so as to be distinguishable from other quantitative values. Besides changing the format of characters, their background color or the like may also be changed. In FIG. 5, quantitative values whereof the display format is modified in this manner are indicated by surrounding with a dotted line box. Namely, FIG. 5 shows that the quantitative value for component B in specimen b is uncertain (requires confirmation of mass spectrum, etc.).

Based on such display, the operator can easily ascertain the combinations of samples and components requiring visual confirmation of mass spectrum and mass chromatogram. Furthermore, preferably, when the characters or a suitable location inside the cell in the table shown in FIG. 5 is clicked with a pointing device such as a mouse, the measured mass spectrum, mass chromatogram, etc. corresponding to that combination of sample and component are extracted into a pop-up window screen that opens automatically. Moreover, the normalized standard mass spectrum obtained in the course of the processing may also be extracted. In this way, by allowing graphs requiring confirmation to be displayed on the screen by means of a simple operation, the operator's effort involved in the graph confirmation operation is reduced, greatly contributing to the improvement of efficiency of analysis operations.

It will be noted that the embodiment example described above is but one example of the present invention, and suitable modifications, alterations or additions within the gist of the present invention are obviously included within the scope of patent claims of the present application. For example, in the embodiment example described above, the present invention was applied to a GC-MS, but it can obviously also be applied to an LC-MS.

EXPLANATIONS OF REFERENCES

1 . . . GC unit
10 . . . sample gasification chamber
11 . . . injector
12 . . . column
13 . . . column oven
2 . . . MS unit
20 . . . ion source
21 . . . quadrupole mass filter
22 . . . ion detector
3 . . . A/D converter
4 . . . data processing unit
41 . . . data collection unit
42 . . . confirmation-required component extraction unit
43 . . . confirmation-required component storage unit
44 . . . quantitation computation unit
45 . . . quantitation results display processing unit
5 . . . measured data storage unit
6 . . . component information storage unit
7 . . . input unit
8 . . . display unit

What is claimed:
1. A chromatography/mass spectrometry device, comprising:
a chromatograph that separates components in a sample in the time direction;
a mass spectrometer that repeatedly performs mass analysis over a predetermined mass/charge ratio range on target components of the separated components; and
an information storage which, for each target component, stores a retention time, standard mass spectrum, multiple characteristic mass/charge ratios which are mass/charge ratios at which characteristic peaks appear on said standard mass spectrum, and an intensity threshold for evaluating peak intensity at a representative mass/charge ratio among said multiple characteristic mass/charge ratios; and
a processor that performs analytical processing of data regarding the target components, the processor configured to for a target component of interest, classify peaks detected on a mass chromatogram at said multiple characteristic mass/charge ratios generated on the basis of data obtained through actual measurement, into one or multiple peak groups according to the occurrence time thereof, and acquire a measured mass spectrum obtained at the appearance time of the peak tops of peaks contained in at least one of those peak groups;

match the measured mass spectrum with the standard mass spectrum corresponding to said target component of interest at each mass/charge ratio, and scale up or scale down the peak intensities of said standard mass spectrum uniformly across the entirety of the mass/charge ratios so as not to exceed the intensities of the peaks on said measured mass spectrum; and on the standard mass spectrum which has been scaled up or scaled down, evaluate whether or not the peak intensity at the representative mass/charge ratio corresponding to said target component of interest exceeds the intensity threshold corresponding to said target component, and use the fact that the peak intensity does exceed the corresponding intensity threshold as a condition for selecting said target component as an unknown component of the sample.

2. The chromatography/mass spectrometry device as described in claim 1,
wherein the target component is selected as the unknown component of the sample if the peak intensity at the representative mass/charge ratio corresponding to said target component of interest exceeds the intensity threshold corresponding to the target component and if a confirmation ion ratio, which is the ratio between the peak intensity at said representative mass/charge ratio and the intensity of peaks at other characteristic mass/charge ratios, is outside a predetermined range.

3. The chromatography/mass spectrometry device as described in claim 1, wherein the processor is further configured to
generate a table listing abundances, or indicator values reflecting abundances, of multiple target components for each sample, and display the table on a screen of a display,
wherein the abundances or indicator values reflecting abundances of target components selected as unknown components of the sample are displayed in a manner distinguishable from the abundances or indicator values reflecting the abundances of other target components.

4. The chromatography/mass spectrometry device as described in claim 1, wherein the processor is further configured to
for the target component selected as the unknown component of the sample, display a mass chromatogram at the representative mass/charge ratio corresponding to the target component on a screen of a display.

5. The chromatography/mass spectrometry device as described in claim 1, wherein the processor is further configured to
for a target component selected as the unknown component of the sample, display the measured mass spectrum on a screen of a display.

6. The chromatography/mass spectrometry device as described in claim 5, wherein the processor is further configured to display a standard mass spectrum which has been scaled up or scaled down along with the measured mass spectrum on a screen of a display.

7. The chromatography/mass spectrometry device as described in claim 1, wherein the peak intensities of said standard mass spectrum are scaled up or scaled down by determining a ratio of a peak intensity on the measured mass spectrum to a peak intensity on the standard mass spectrum for the mass/charge ratios of all peaks present on the standard mass spectrum of the target component, and then selecting the smallest ratio as a scaling factor used to scale up or scale down the peak intensities of said standard mass spectrum.

8. A chromatography/mass spectrometry method, comprising:
separating components in a sample in the time direction using a chromatograph;
repeatedly performing mass analysis over a predetermined mass/charge ratio range on target components of the separated components using a mass spectrometer; and
for each target component, storing in an information storage unit a retention time, standard mass spectrum, multiple characteristic mass/charge ratios, which are mass/charge ratios at which characteristic peaks appear on said standard mass spectrum, and an intensity threshold for evaluating peak intensity at a representative mass/charge ratio among said multiple characteristic mass/charge ratios; and
performing analytical processing of data regarding the target components by
for a target component of interest, classifying peaks detected on a mass chromatogram at said multiple characteristic mass/charge ratios generated on the basis of data obtained through actual measurement, into one or multiple peak groups according to the occurrence time thereof, and acquiring a measured mass spectrum obtained at the appearance time of the peak tops of peaks contained in at least one of those peak groups;
matching the measured mass spectrum with the standard mass spectrum corresponding to said target component of interest at each mass/charge ratio, and scaling up or scales down the peak intensities of said standard mass spectrum uniformly across the entirety of the mass/charge ratios so as not to exceed the intensities of the peaks on said measured mass spectrum; and
on the standard mass spectrum which has been scaled up or scaled down, evaluating whether or not the peak intensity at the representative mass/charge ratio corresponding to said target component of interest exceeds the intensity threshold corresponding to said target component, and using the fact that the peak intensity does exceed the corresponding intensity threshold as a condition for selecting said target component as an unknown component of the sample.

9. The chromatography/mass spectrometry method as described in claim 8,
wherein the target component is selected as the unknown component of the sample if the peak intensity at the representative mass/charge ratio corresponding to said target component of interest exceeds the intensity threshold corresponding to the target component and if a confirmation ion ratio, which is the ratio between the peak intensity at said representative mass/charge ratio and the intensity of peaks at other characteristic mass/charge ratios, is outside a predetermined range.

10. The chromatography/mass spectrometry method as described in claim 8,
further comprising generating a table listing abundances, or indicator values reflecting abundances, of multiple target components for each sample, and displaying the table on a screen of a display,
wherein the abundances or indicator values reflecting abundances of target components selected as unknown components of the sample components are displayed in a manner distinguishable from the abundances or indicator values reflecting the abundances of other target components.

11. The chromatography/mass spectrometry method as described in claim 8,
further comprising displaying a mass chromatogram for the target component selected as the unknown component of the sample at the representative mass/charge ratio corresponding to the target component on a screen of a display.

12. The chromatography/mass spectrometry method as described in claim 8,
further comprising displaying the measured mass spectrum for the target component selected as the unknown component of the sample on a screen of a display.

13. The chromatography/mass spectrometry method as described in claim 12,
wherein a standard mass spectrum which has been scaled up or scaled down along with the measured mass spectrum on a screen of a display.

14. The chromatography/mass spectrometry method as described in claim 8, wherein the peak intensities of said standard mass spectrum are scaled up or scaled down by determining a ratio of a peak intensity on the measured mass spectrum to a peak intensity on the standard mass spectrum for the mass/charge ratios of all peaks present on the standard mass spectrum of the target component, and then selecting the smallest ratio as a scaling factor used to scale up or scale down the peak intensities of said standard mass spectrum.

* * * * *